United States Patent [19]

Miege et al.

[11] Patent Number: 4,976,534
[45] Date of Patent: Dec. 11, 1990

[54] SIMULTANEOUS VISION OPTICAL LENS FOR CORRECTING PRESBYOPIA

[75] Inventors: Christian Miege, Eaubonne; Pierre Monteil, Paris; Gerard Obrecht, Les Moulineaux, all of France

[73] Assignee: Essilor International, Cie Generale D'Optique, Creteil Cedex, France

[21] Appl. No.: 468,282

[22] Filed: Jan. 22, 1990

[30] Foreign Application Priority Data

Feb. 3, 1989 [FR] France ................... 89 01417

[51] Int. Cl.⁵ ................... G02C 7/04; A61F 2/16
[52] U.S. Cl. ................... 351/161; 623/5; 623/6
[58] Field of Search ............ 351/160 R, 160 H, 161, 351/162; 623/5, 6

[56] References Cited

U.S. PATENT DOCUMENTS

| | | | |
|---|---|---|---|
| 4,199,231 | 4/1980 | Evans | 351/161 X |
| 4,418,991 | 12/1983 | Breger | 351/161 |
| 4,704,016 | 11/1987 | DeCarle | 351/161 |
| 4,778,462 | 10/1988 | Grendahl | 351/161 X |
| 4,795,462 | 1/1989 | Grendahl | 351/161 X |
| 4,798,609 | 1/1989 | Grendahl | 351/161 X |

FOREIGN PATENT DOCUMENTS

| | | | |
|---|---|---|---|
| 0169599 | 1/1986 | European Pat. Off. | 351/161 |
| 2139375 | 11/1984 | United Kingdom | 351/161 |

Primary Examiner—Scott J. Sugarman
Attorney, Agent, or Firm—Charles E. Brown; Charles A. Brown

[57] ABSTRACT

The proximity P of a simultaneous vision optical lens for correcting presbyopia is defined as the reciprocal of the distance D at which a light ray parallel to and at a distance h from its axis crosses the axis after passing through the lens. The curve representing the proximity P of the lens lies between a lower envelope curve $P_{inf}$ and an upper envelope curve $P_{sup}$ satisfying the following equations:

$$P_{inf} = f(h) = (\Sigma A'_i h^i) + P_{VL}$$

$$P_{sup} = f(h) = (\Sigma A''_i h^i) + P_{VL}$$

in which $P_{VL}$ is the proximity for distant vision and $A'_i$, $A''_i$ are numeric coefficients depending on the proximity addition added for near vision to the proximity for far vision. The lens may be implemented as a contact lens, an intra-ocular implant or an intra-corneal lens.

5 Claims, 2 Drawing Sheets

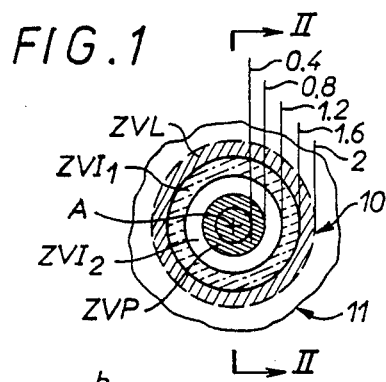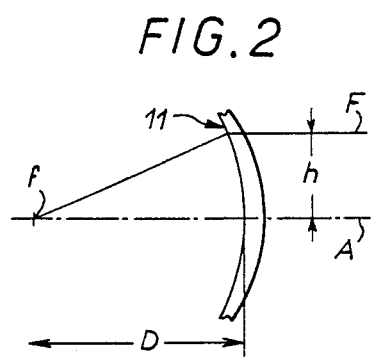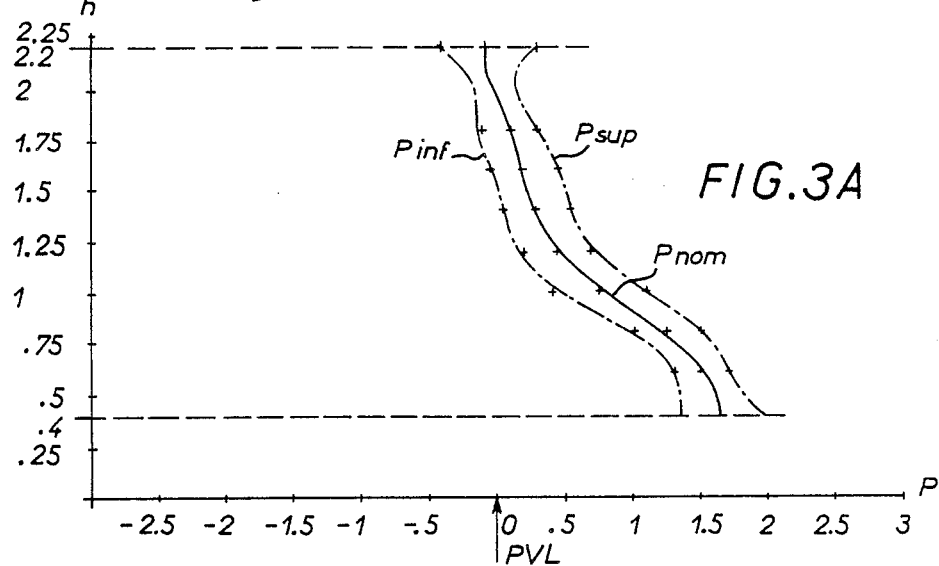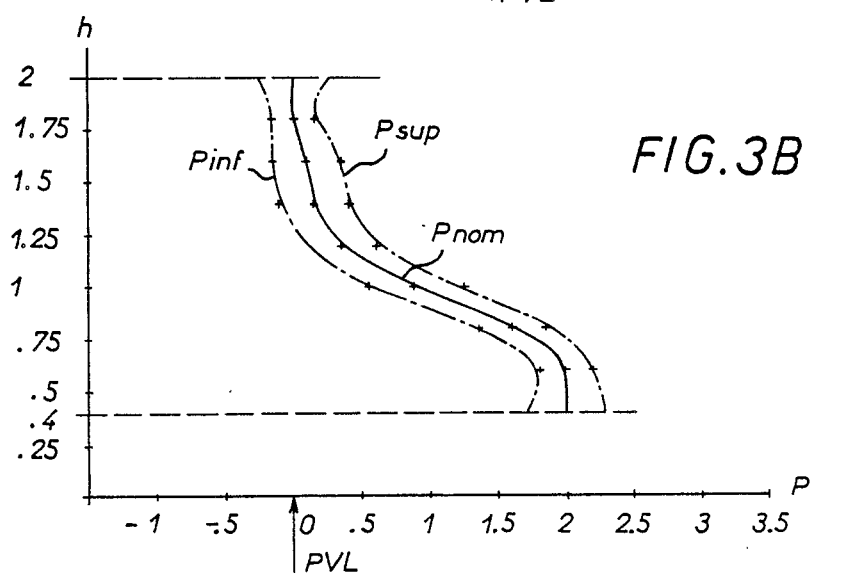

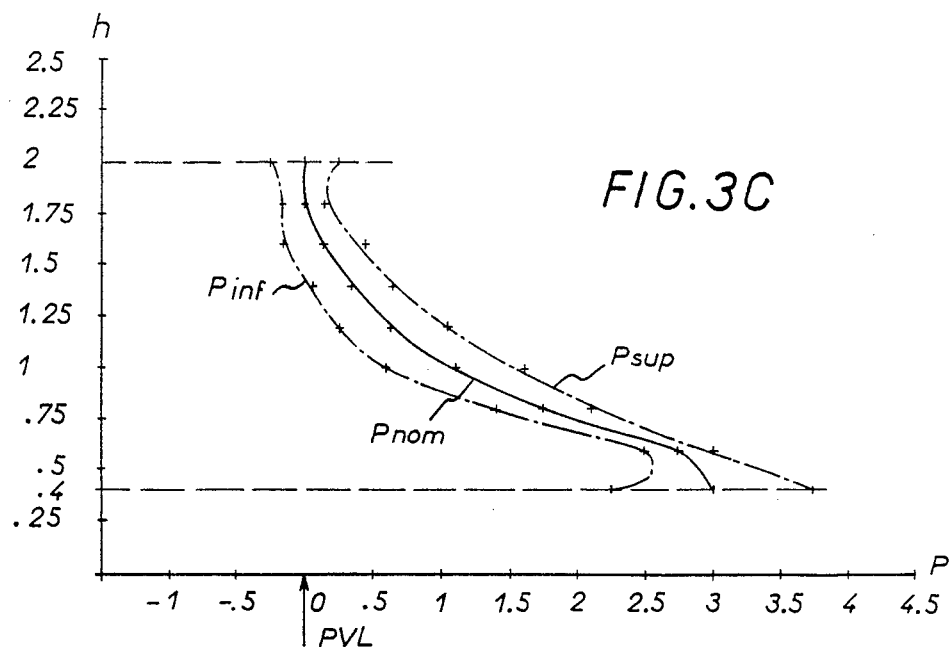
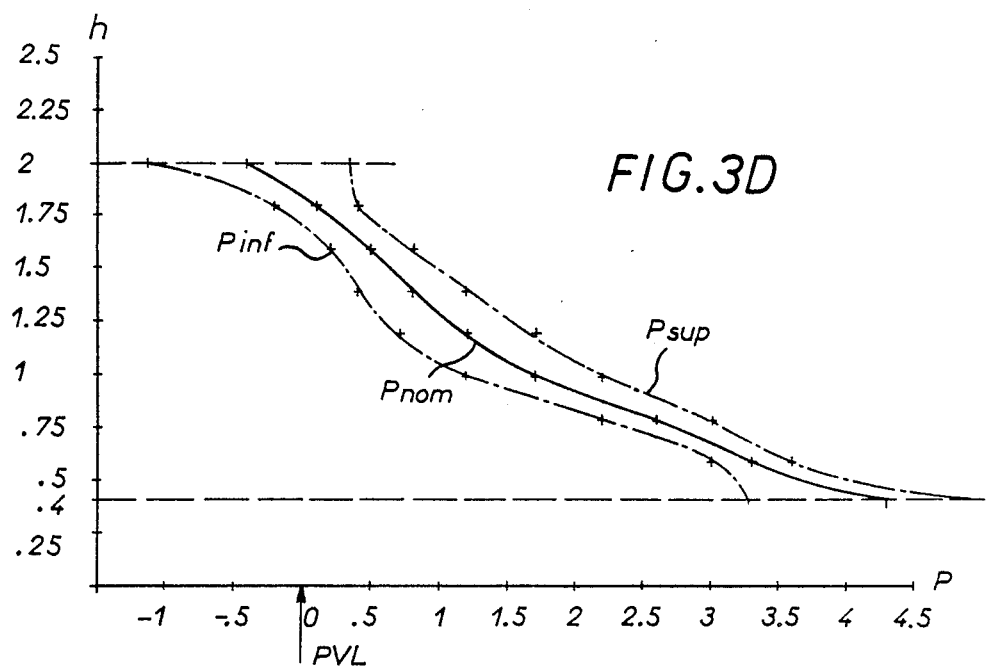

1

SIMULTANEOUS VISION OPTICAL LENS FOR CORRECTING PRESBYOPIA

BACKGROUND OF THE INVENTION

1. Field of the Invention

The present invention concerns an optical lens for correcting presbyopia, that is to say a lens for compensating defective accommodation of the crystalline lens, the accommodation capability of which decreases with age.

2. Description of the Prior Art

An optical lens of this kind must enable the wearer to see clearly an object at any distance (far away, intermediate distance or near).

The present lens is of the progressive simultaneous vision kind in which the non-optical central part, which has a diameter substantially equal (at low light levels) to that of the pupil, comprises respective annular areas for far vision, intermediate vision and near vision, with the near vision area inside the far vision area or vice-versa.

It may be a contact lens or an intra-ocular implant or an intra-corneal lens.

A unifocal optical lens is usually characterized by its power in diopters which is the reciprocal of its focal length, all incident light rays parallel to its optical axis passing through its focus irrespective of their initial distance from this axis.

A bifocal optical lens with two well-defined concentric areas has two corresponding separate powers, one for correcting ametropia in far vision and the other for compensating presbyopia in near vision. The difference between these two powers is referred to as the "addition".

Strictly speaking, however, in the case of a progressive simultaneous vision lens these power characteristics (which from the wearer's point of view represent the ophthalmic requirements for satisfactory sight) are more or less wanting, the useful optical area of a progressive lens of this kind having no stable power characteristics, strictly speaking.

For this reason the term "proximity" is used hereinafter rather than the term "power" to refer to the reciprocal of the distance at which a light ray parallel to the optical axis of the lens crosses the axis after passing though the lens.

In practise the proximity of an optical lens for a person with presbyopia must have at least two distinct ranges of values appropriate to the changing visual requirements of the wearer, namely a range of values specifically intended for far vision and a range of values specifically intended for near vision, the latter being deduced from the former by adding a specific "addition" with continuous intermediate joining values between these values, the whole representing a particular law of evolution determined in each case.

The problem is that, given the theoretically ideal solution of a rapid change between the proximity value for far vision and its value for near vision, there is no law of evolution universally applicable to obtain good results for all persons, the best law of evolution for each person depending in particular on the addition needed by that person.

A linear or quasi-linear addition law, for example, or a single law whatever the addition, does not give good results in practise, the wearer not seeing particularly well either far away or near.

The present invention is based on the new discovery that it is possible to achieve good results systematically by making the curve representing the proximity as a function of the distance from the axis fit within specific limits characteristic of the addition needed by the wearer.

SUMMARY OF THE INVENTION

The invention consists in a progressive simultaneous vision optical lens for correcting presbyopia in which the curve representing its proximity P defined as the reciprocal in diopters of the distance D at which a light ray parallel to and at a distance h from its axis crosses the axis after passing through the lens lies within an area between a lower envelope curve $P_{inf}$ and an upper envelope curve $P_{sup}$ defined by nth and hth degree polynomials and satisfying the following equations:

$$P_{inf} = f(h) = (\Sigma A'_i h^i) + P_{VL}$$

$$P_{sup} = f(h) = (\Sigma A''_i h^i) + P_{VL} \qquad (I)$$

in which $P_{VL}$ is the proximity needed for far vision and $A'_i$, $A''_i$ are the coefficients of the various polynomials depending on the value of the proximity addition $\delta_1 = A_{DD}$ corresponding to the degree of presbyopia of the wearer, the values of these coefficients being substantially as follows:

| for $A_{DD} = 1.5$ D: | |
|---|---|
| A'0 = 12.532267 | A''0 = 16.9452 |
| A'1 = −92.695892 | A''1 = −106.8394 |
| A'2 = 305.16919 | A''2 = 302.62347 |
| A'3 = −513.44922 | A''3 = −443.97601 |
| A'4 = 476.63852 | A''4 = 362.53815 |
| A'5 = −247.99097 | A''5 = −166.29979 |
| A'6 = 67.868942 | A''6 = 40.015385 |
| A'7 = −7.6131396 | A''7 = −3.9203446 |
| for $A_{DD} = 2$ D: | |
| A'0 = 23.56555 | A''0 = 14.368889 |
| A'1 = −182.77804 | A''1 = −87.219223 |
| A'2 = 605.05684 | A''2 = 244.35987 |
| A'3 = −1 024.1053 | A''3 = −337.92626 |
| A'4 = 962.99613 | A''4 = 241.37509 |
| A'5 = −511.24120 | A''5 = −85.757212 |
| A'6 = 143.7355 | A''6 = 12.008102 |
| A'7 = −16.663562 | |
| for $A_{DD} = 2.5$ D: | |
| A'0 = −28.307575 | A''0 = 2.874459 |
| A'1 = 190.37743 | A''1 = 11.541159 |
| A'2 = −445.545294 | A''2 = −35.715782 |
| A'3 = 512.44763 | A''3 = 37.849808 |
| A'4 = −315.3125 | A''4 = −19.0199096 |
| A'5 = 99.678413 | A''5 = 4.2867818 |
| A'6 = −12.731333 | A''6 = −0.28934118 |
| for $A_{DD} = 3$ D: | |
| A'0 = 22.19555 | A''0 = 57.071102 |
| A'1 = −157.74065 | A''1 = −357.09277 |
| A'2 = 529.74104 | A''2 = 1 000.8899 |
| A'3 = −918.56382 | A''3 = −1 509.5112 |
| A'4 = 881.73279 | A''4 = 1 311.576 |
| A'5 = −475.73774 | A''5 = −657.94254 |
| A'6 = 135.48897 | A''6 = 177.01095 |
| A'7 = −15.888513 | A''7 = −19.763759 | and, for possible intermediate additions whose value $\delta$ is between two above-mentioned addition values $\delta_1$ and $\delta_1 + 0.5$, the envelope curves of these intermediate additions are deduced from the envelope curves corresponding to $\delta_1$ and $\delta_1 + 0.5$ by the equations:

$$P^{\delta}_{inf}(h) = \left(\frac{\delta - \delta_1}{0.5}\right)\Delta P_{inf} + P^{\delta_1}_{inf}$$

$$P^{\delta}_{sup}(h) = \left(\frac{\delta - \delta_1}{0.5}\right)\Delta P_{sup} + P^{\delta_1}_{sup}$$

with $\Delta P_{inf} = P^{\delta_1+0.5}_{inf} - P^{\delta_1}_{inf}$ $\Delta P_{sup} = P^{\delta_1+0.5}_{sup} - P^{\delta_1}_{sup}.$ Experience shows that complying with the above decreasing monotonic continuous limiting curves (I) yields highly satisfactory results for any wearer whatever addition they need.

The characteristics and advantages of the invention will emerge from the following description given by way of example with reference to the appended diagrammatic drawings.

BRIEF DESCRIPTION OF THE DRAWINGS

FIG. 1 is a partial plan view of an optical lens in accordance with the invention.

FIG. 2 is a partial view of it in axial cross-section on the line II—II in FIG. 1.

FIG. 3A is a diagram showing the proximity of this optical lens for a first value of its addition.

FIGS. 3B through 3D are diagrams analogous to that of FIG. 3A for other values of the addition.

DETAILED DESCRIPTION OF THE INVENTION

As schematically represented in FIG. 1, the useful optical area 10 of the lens 11 in accordance with the invention is entirely confined within a circumference of fixed radius appropriate to the addition: 2.2 mm for the addition 1.5 D and 2 mm for the additions 2 D, 2.5 D and 3 D. For the same luminance conditions the radius of the human pupil decreases with age. Its value is related to the addition needed by the wearer and for a person with presbyopia is generally 2.2 mm or less.

A denotes the axis of the lens 11.

As in the example described this is a convergent lens, any incident light ray F parallel to the axis A at a distance h from the axis A crosses the axis A after passing through the lens 11 at a point f at a distance D from the lens.

The proximity P in diopters is the reciprocal of this distance in m.

If the distance h is greater than 2.2 mm or 2 mm the incident light rays are stopped by the pupil and do not in practise contribute to forming an image.

This is why in the example described the useful area 10 of the lens 11 is limited peripherally to a circumference with a radius of 2 mm.

For practical reasons, and as schematically shown in dashed outline in FIG. 1, this useful area 10 is also delimited, near the axis A, by a circumference with a radius of 0.4 mm. It must be understood that the surface of the central area offset in this way represents only a minimal fraction (not exceeding 4%) of the total surface area. Within this central area, however, the curves $P_{inf}$ (h) and $P_{sup}$ (h) are nevertheless continuous with the previous curves.

As schematically represented by the shading in FIG. 1, the useful area 10 comprises four separate concentric annular vision areas, namely a far vision area $Z_{VL}$, two intermediate vision areas $Z_{VI1}$ and $Z_{VI2}$ and a near vision area $Z_{VP}$.

In the embodiment shown, which is a preferred embodiment, the areas $Z_{VL}$, $Z_{VI1}$, $Z_{VI2}$ and $Z_{VP}$ extend from the edge of the useful area 10 towards its central area.

The converse arrangement can be used if required, however.

For convenience, and for reasons which will emerge later, it will be assumed hereinafter that the near vision area $Z_{VP}$ lies between 0.4 mm and 0.8 mm and that the far vision area $Z_{VL}$ lies between 1.6 mm and 2 or 2.2 mm.

According to the invention, the curve representing the proximity P as a function of the distance h lies within an area between a lower envelope curve $P_{inf}$ and an upper envelope $P_{sup}$ satisfying the following equations:

$$P_{inf}=f(h)=(\Sigma A'_i h^i)+P_{VL}$$

$$P_{sup}=f(h)=(\Sigma A''_i h^i)+P_{VL} \qquad (I)$$

in which $P_{VL}$ is the proximity needed for far vision and $A'_i$, $A''_i$ are the coefficients of the various polynomials depending on the value of the proximity addition $\delta_1 = A_{DD}$ corresponding to the degree of presbyopia of the wearer, the values of these coefficients being substantially as follows:

| for $A_{DD}$ = 1.5 D: | |
|---|---|
| A'0 = 12.532267 | A''0 = 16.9452 |
| A'1 = −92.695892 | A''1 = −106.8394 |
| A'2 = 305.16919 | A''2 = 302.62347 |
| A'3 = −513.44922 | A''3 = −443.97601 |
| A'4 = 476.63852 | A''4 = 362.53815 |
| A'5 = −247.99097 | A''5 = −166.29979 |
| A'6 = 67.868942 | A''6 = 40.015385 |
| A'7 = −7.6131396 | A''7 = −3.9203446 |
| for $A_{DD}$ = 2 D: | |
| A'0 = 23.56555 | A''0 = 14.368889 |
| A'1 = −182.77804 | A''1 = −87.219223 |
| A'2 = 605.05684 | A''2 = 244.35987 |
| A'3 = −1 024.1053 | A''3 = −337.92626 |
| A'4 = 962.99613 | A''4 = 241.37509 |
| A'5 = −511.24120 | A''5 = −85.757212 |
| A'6 = 143.7355 | A''6 = 12.008102 |
| A'7 = −16.663562 | |
| for $A_{DD}$ = 2.5 D: | |
| A'0 = −28.307575 | A''0 = 2.874459 |
| A'1 = 190.37743 | A''1 = 11.541159 |
| A'2 = −445.545294 | A''2 = −35.715782 |
| A'3 = 512.44763 | A''3 = 37.849808 |
| A'4 = −315.3125 | A''4 = −19.0199096 |
| A'5 = 99.678413 | A''5 = 4.2867818 |
| A'6 = −12.731333 | A''6 = −0.28934118 |
| for $A_{DD}$ = 3 D: | |
| A'0 = 22.19555 | A''0 = 57.071102 |
| A'1 = −157.74065 | A''1 = −357.09277 |
| A'2 = 529.74104 | A''2 = 1 000.8899 |
| A'3 = −918.56382 | A''3 = −1 509.5112 |
| A'4 = 881.73279 | A''4 = 1 311.576 |
| A'5 = −475.73774 | A''5 = −657.94254 |
| A'6 = 135.48897 | A''6 = 177.01095 |
| A'7 = −15.888513 | A''7 = −19.763759 | and, for possible intermediate additions whose value $\delta$ is between two above-mentioned addition values $\delta_1$ and $\delta_1+0.5$, the envelope curves of these intermediate additions are deduced from the envelope curves corresponding to $\delta_1$ and $\delta_1+0.5$ by the equations:

$$P^\delta_{inf}(h) = \left(\frac{\delta - \delta 1}{0.5}\right)\Delta P_{inf} + P^{\delta 1}_{inf}$$

$$P^\delta_{sup}(h) = \left(\frac{\delta - \delta 1}{0.5}\right)\Delta P_{sup} + P^{\delta 1}_{sup}$$

with $\Delta P_{inf} = P^{\delta 1+0.5}_{inf} - P^{\delta 1}_{inf}$ $\Delta P_{sup} = P^{\delta 1+0.5}_{sup} - P^{\delta 1}_{sup}.$ The proximity curve of an ophthalmic lens is one characteristic of the lens and it is therefore possible to identify an optical lens by determining the proximity curve using appropriate analysis means.

Starting from a proximity curve of this kind it is possible to determine the surfaces required for the front and rear of the optical lens so that it satisfies this proximity curve.

As the corresponding techniques are within the competence of those skilled in the art they will not be described here.

The rear of the optical lens 11 in accordance with the invention may be a part-spherical surface, for example, only the front surface having to be adapted to provide the necessary proximity curve.

Any combination of spherical or aspherical surfaces giving a proximity curve within the previously described limits is feasible.

In the diagrams of FIGS. 3A through 3D the proximity P in diopters is plotted against the distance h in millimeters and there are shown in chain-dotted outline the respective envelope curves $P_{inf}$, $P_{sup}$ (I) corresponding, for a distant vision proximity value $P_{VL}$ equal to 0, to a proximity addition $A_{DD}$ equal to 1.5 for FIG. 3A, equal to 2 for FIG. 3B, equal to 2.5 for FIG. 3C and equal to 3 for FIG. 3D.

For other, positive or negative values of $P_{VL}$ the $P_{inf}(h)$ and $P_{sup}(h)$ curves can be deduced by simple translation.

These diagrams also show in full line between the envelope curves $P_{inf}$, $P_{sup}$ a nominal curve $P_{nom}$ which is particularly satisfactory.

The nominal curve $P_{nom}$ satisfies the following equation:

$$P_{nom} = f(h) = (\Sigma A_i h^i) + P_{VL}$$

with values for the numeric coefficients $A_i$ substantially equal to the following values:

| | |
|---|---|
| for $A_{DD} =$ | 1.5 D: |
| A0 = | 1.8983333 |
| A1 = | −3.8368794 |
| A2 = | 17.797017 |
| A3 = | −34.095052 |
| A4 = | 28.027344 |
| A5 = | −10.464243 |
| A6 = | 1.464837 |
| A7 = | 0 |
| for $A_{DD} =$ | 2 D |
| A0 = | 12.637321 |
| A1 = | −85.632629 |
| A2 = | 269.61975 |
| A3 = | −425.09732 |
| A4 = | 361.26779 |
| A5 = | −168.43481 |
| A6 = | 40.408779 |
| A7 = | −3.8719125 |
| for $A_{DD} =$ | 2.5 D |

-continued

| | |
|---|---|
| A0 = | −12.716558 |
| A1 = | 100.95929 |
| A2 = | −240.63054 |
| A3 = | 275.14871 |
| A4 = | −167.1658 |
| A5 = | 51.982597 |
| A6 = | −6.5103369 |
| for $A_{DD} =$ | 3 D |
| A0 = | 39.633326 |
| A1 = | −257.41671 |
| A2 = | 765.31546 |
| A3 = | −1 214.0375 |
| A4 = | 1 096.6544 |
| A5 = | −566.84014 |
| A6 = | 156.24996 |
| A7 = | −17.826136 |

It will be noted that at least in the central part the lower envelope curve $P_{inf}$ and the upper envelope curve $P_{sup}$ are generally similar to the corresponding nominal curve $P_{nom}$.

Along one of the proximity curves shown in the diagrams of FIGS. 3A through 3D the local value of the proximity gradient dP/dH preferably does not exceed 5 D/mm continuously over a range of proximity greater than 0.25 D (II).

As can be seen in the figures, the proximity corresponding to the lower limit of the useful area 10 has a value greater than $(P_{VL} + A_{DD})$.

Preferably, and as shown in FIGS. 3A through 3D, the average proximity gradient $G_{VP}$ for near vision as evaluated only from the coordinates of points on the nominal curve $P_{nom}$ corresponding to the above-specified limits of the near vision area $Z_{VP}$ and the mean proximity gradient $G_{VL}$ for distant vision, similarly evaluated, are related as follows:

$$G_{VP}/G_{VL} > 2 \tag{III}$$

Preferably, and as in the embodiment shown, the surface $S_{VP}$ of the transition section contributing usefully to near vision, in practise the surface of the near vision area $S_{VP}$, and the surface $S_{VL}$ of the transition section contributing usefully to distant vision, in practise the surface of the distant vision area $Z_{VL}$, are related as follows:

$$S_{VL}/S_{VP} \geq 3 \tag{IV}$$

Experience shows that the characteristics II, III and IV yield good results.

Of course, the present invention is not limited to the embodiment described and shown but encompasses any variant execution thereof.

We claim:

1. Progressive simultaneous vision optical lens for correcting presbyopia in which the curve representing its proximity P defined as the reciprocal in diopters of the distance D at which a light ray parallel to and at a distance h from its axis crosses the axis after passing through the lens lies within an area between a lower envelope curve $P_{inf}$ and an upper envelope curve $P_{sup}$ defined by nth and hth degree polynomials and satisfying the following equations:

$$P_{inf} = f(h) = (\Sigma A'_i h^i) + P_{VL}$$

$$P_{sup} = f(h) = (\Sigma A''_i h^i) + P_{VL} \tag{I}$$

in which $P_{VL}$ is the proximity needed for far vision and $A'_i$, $A''_i$ are the coefficients of the various polynomials depending on the value of the proximity addition $\delta_1 = A_{DD}$ corresponding to the degree of presbyopia of the wearer, the values of these coefficients being substantially as follows:

| for $A_{DD}$ = 1.5 D: | |
|---|---|
| A'0 = 12.532267 | A''0 = 16.9452 |
| A'1 = −92.695892 | A''1 = −106.8394 |
| A'2 = 305.16919 | A''2 = 302.62347 |
| A'3 = −513.44922 | A''3 = −443.97601 |
| A'4 = 476.63852 | A''4 = 362.53815 |
| A'5 = −247.99097 | A''5 = −166.29979 |
| A'6 = 67.868942 | A''6 = 40.015385 |
| A'7 = −7.6131396 | A''7 = −3.9203446 |
| for $A_{DD}$ = 2 D: | |
| A'0 = 23.56555 | A''0 = 14.368889 |
| A'1 = −182.77804 | A''1 = −87.219223 |
| A'2 = 605.05684 | A''2 = 244.35987 |
| A'3 = −1 024.1053 | A''3 = −337.92626 |
| A'4 = 962.99613 | A''4 = 241.37509 |
| A'5 = −511.24120 | A''5 = −85.757212 |
| A'6 = 143.7355 | A''6 = 12.008102 |
| A'7 = −16.663562 | |
| for $A_{DD}$ = 2.5 D: | |
| A'0 = −28.307575 | A''0 = 2.874459 |
| A'1 = 190.37743 | A''1 = 11.541159 |
| A'2 = −445.545294 | A''2 = −35.715782 |
| A'3 = 512.44763 | A''3 = 37.849808 |
| A'4 = −315.3125 | A''4 = −19.0199096 |
| A'5 = 99.678413 | A''5 = 4.2867818 |
| A'6 = −12.731333 | A''6 = −0.28934118 |
| for $A_{DD}$ = 3 D: | |
| A'0 = 22.19555 | A''0 = 57.071102 |
| A'1 = −157.74065 | A''1 = −357.09277 |
| A'2 = 529.74104 | A''2 = 1 000.8899 |
| A'3 = −918.56382 | A''3 = −1 509.5112 |
| A'4 = 881.73279 | A''4 = 1 311.576 |
| A'5 = −475.73774 | A''5 = −657.94254 |
| A'6 = 135.48897 | A''6 = 177.01095 |
| A'7 = −15.888513 | A''7 = −19.763759 | and, for possible intermediate additions whose value $\delta$ is between two above-mentioned addition values $\delta_1$ and $\delta_1 + 0.5$, the envelope curves of these intermediate additions are deduced from the envelope curves corresponding to $\delta_1$ and $\delta_1 + 0.5$ by the equations:

$$P^\delta_{inf}(h) = \left(\frac{\delta - \delta_1}{0.5}\right)\Delta P_{inf} + P^{\delta_1}_{inf}$$

$$P^\delta_{sup}(h) = \left(\frac{\delta - \delta_1}{0.5}\right)\Delta P_{sup} + P^{\delta_1}_{sup}$$

with $\Delta P_{inf} = P^{\delta_1 + 0.5}_{inf} - P^{\delta_1}_{inf}$ $$\Delta P_{sup} = P^{\delta_1 + 0.5}_{sup} - P^{\delta_1}_{sup}.$$

2. Optical lens according to claim 1 wherein the curve representative of its proximity satisfies the following equation:

$$P_{nom} = f(h) = (\Sigma A_i h^i) + P_{VL}$$

with, subject to the same conditions as previously:

| for $A_{DD}$ = | 1.5 D: |
|---|---|
| A0 = | 1.8983333 |
| A1 = | −3.8368794 |
| A2 = | 17.797017 |
| A3 = | −34.095052 |
| A4 = | 28.027344 |
| A5 = | −10.464243 |
| A6 = | 1.464837 |
| A7 = | 0 |
| for $A_{DD}$ = | 2 D |
| A0 = | 12.637321 |
| A1 = | −85.632629 |
| A2 = | 269.61975 |
| A3 = | −425.09732 |
| A4 = | 361.26779 |
| A5 = | −168.43481 |
| A6 = | 40.408779 |
| A7 = | −3.8719125 |
| for $A_{DD}$ = | 2.5 D |
| A0 = | −12.716558 |
| A1 = | 100.95929 |
| A2 = | −240.63054 |
| A3 = | 275.14871 |
| A4 = | −167.1658 |
| A5 = | 51.982597 |
| A6 = | −6.5103369 |
| for $A_{DD}$ = | 3 D |
| A0 = | 39.633326 |
| A1 = | −257.41671 |
| A2 = | 765.31546 |
| A3 = | −1 214.0375 |
| A4 = | 1 096.6544 |
| A5 = | −566.84014 |
| A6 = | 156.24996 |
| A7 = | −17.826136 |

3. Optical lens according to claim 1 wherein the local value of the proximity gradient dP/dh does not exceed 5 diopters per millimeter continuously over a proximity range greater than 0.25 diopters.

4. Optical lens according to claim 1 wherein the mean proximity gradient $G_{VP}$ for near vision and the mean proximity gradient $G_{VL}$ for distant vision are related as follows:

$G_{VP}/G_{VL} > 2$.

5. Ophthalmic lens according to claim 1 wherein the surface $S_{VP}$ of the transition area contributing usefully to near vision and the surface $S_{VL}$ of the transition area contributing usefully to far vision are related as follows:

$S_{VL}/S_{VP} \geq 3$.

* * * * *